United States Patent [19]

Cheh et al.

[11] Patent Number: 4,732,581
[45] Date of Patent: Mar. 22, 1988

[54] GAS CHROMATOGRAPHIC METHOD FOR SEPARATING HYDROGEN ISOTOPES

[76] Inventors: Christopher H. Cheh, 4239 Anworld Place, Mississauga, Ontario, Canada, L4W 2W1; Ronald E. Massey, 3135 Bentworth Drive, Burlington, Ontario, Canada, L7M 1V9; Otto K. Kveton, 25 Dacre Crescent, Toronto, Ontario, Canada, M6S 2W2; Samuel H. Hawthorne, 3 Farmington Drive, Brampton, Ontario, Canada, L6W 2V1; Savtantar K. Sood, 97 Banting Crescent, Brampton, Ontario, Canada, L6Y 2M3

[21] Appl. No.: 861,336

[22] Filed: May 8, 1986

[51] Int. Cl.[4] .............................................. B01D 15/08
[52] U.S. Cl. ............................................ 55/67; 55/75; 55/197; 55/386
[58] Field of Search ................... 55/67, 68, 75, 197, 55/386

[56] References Cited

U.S. PATENT DOCUMENTS

| | | | |
|---|---|---|---|
| 3,011,589 | 12/1961 | Meyer | 55/75 X |
| 3,043,127 | 7/1962 | Deford et al. | 55/67 X |
| 3,488,921 | 1/1970 | Inchauspe | 55/67 X |
| 3,524,305 | 8/1970 | Ives | 55/386 |
| 3,769,776 | 11/1973 | Berg | 55/67 |
| 3,843,518 | 10/1974 | Magee et al. | 55/67 X |
| 4,271,697 | 6/1981 | Mowery, Jr. | 55/67 X |
| 4,276,060 | 6/1981 | Aldridge | 55/67 |
| 4,470,832 | 9/1984 | Sugawara et al. | 55/197 |

FOREIGN PATENT DOCUMENTS

| | | | |
|---|---|---|---|
| 1241416 | 6/1967 | Fed. Rep. of Germany | 55/67 |
| 2024648 | 1/1980 | United Kingdom | 55/67 |

Primary Examiner—Robert Spitzer
Attorney, Agent, or Firm—Ridout & Maybee

[57] ABSTRACT

A method for separating hydrogen isotope species by gas chromatography is described. The invention utilizes low temperature chromatography on molecular sieves with peak cutting or temperature programming depending on the particular application. The method provides a much larger throughput capability than was heretofore available. The invention also includes the separation of mixed dimer isotope species from the helium carrier gas by condensation, and storage thereof at low temperature in a non-catalytic environment so that equilibration may be avoided.

31 Claims, 6 Drawing Figures

FIG. 3c (c) Peak Cutting Operation

FIG. 4

GAS CHROMATOGRAPHIC METHOD FOR SEPARATING HYDROGEN ISOTOPES

The present invention relates to a method for separating the isotopic species of hydrogen on a moderately large scale using low temperature gas chromatography. The invention is addressed principally to those applications where a sufficient amount of material is not available to warrant a separation by cryogenic distillation.

The invention may be used to separate and store all six dimeric isotope species of hydrogen, i.e. $H_2$, HD, HT, $D_2$, DT, $T_2$, or to obtain partial separation of one or more components from a mixture by using peak cutting techniques. The capacity or throughput possible by use of the present method is much greater than that previously available without sacrificing the high separation efficiency obtainable by gas chromatography. The invention has particular application for fusion fuel clean-up, that is, for the purpose of removing protium containing species from the deuterium and tritium mixture used in fusion studies and which will ultimately be used in fusion reactors.

While cryogenic distillation has been known and used for the purpose of separating isotopic mixtures of hydrogen, this technique is only suitable for use on a large scale. Distillation suffers from the disadvantages of providing a low separation efficiency as well as requiring the retention of a fairly large inventory of material in the distillation system. On the other hand, gas chromatography provides a high separation efficiency and leaves no inventory of desired material in the system, but generally, gas chromatography of hydrogen isotope mixtures has been utilized previously as an analytical tool.

One approach for the development of a large scale gas chromatographic process for separating hydrogen isotopes has been taken by a group at Max Planck Institute in Germany, and is described in U.S. Pat. No. 4,469,496 dated Sept. 4, 1984. Essentially, the approach described in this patent involves increasing the diameter and length of the chromatography column and using up to 5% by volume of an inert fibrous filler material in the column packing. The patent states that separation efficiency is affected by factors such as column cross section, column length, carrier gas velocity and column packing. However, according to the patent teachings, these various factors can be balanced or adjusted to give wholly satisfactory separations of hydrogen isotope mixtures of up to about 500 ml using a column having an internal diameter of 50 mm and length of 3 m. The Max Planck columns are packed with a pre-treated alumina powder. Separation times of 80 to 120 min. were reported by them in Nuclear Tech/Fusion, 4, 687 (1983) for this system giving a throughput of 250-375 ml/h which may be written as 50-75 ml/h/1 cm column.

The present invention has resulted from a different approach taken for the development of a large scale gas chromatography process. In addition to the factors effecting separation efficiency which are mentioned in U.S. Pat. No. 4,469,496, the present process may utilize temperature programming and may employ a plurality of columns to achieve peak cutting. These techniques enable the throughput of a gas chromatography system to be significantly increased in comparison to the prior art without sacrificing separation efficiency, and therefore, allow much more material to be processed without increasing the diameter and length of the columns used.

Thus, the present invention allows a throughput of about 1.8 L/h for fusion fuel clean up using a first column of 8 mm internal diameter and length of 60 cm in series with a second column of 8 mm internal diameter and length of 150 cm, both columns being packed with molecular sieves.

The invention also provides a method for obtaining separation of all six hydrogen isotope species using a temperature program for the chromatography on a single column packed with molecular sieves. This process of the invention yields a throughput of about 380 ml/h/1 cm column or more than 5 times that of the Max Planck system.

Accordingly, the present invention provides a gas chromatographic method for separating one or more minor components from one or more major components of an isotopic mixture of hydrogen, comprising:

injecting a volume of the mixture at a first end of a first of a plurality of columns which are packed with a molecular sieve material, each column being maintained at a temperature of from about $-180°$ C. to about $-140°$ C.;

causing the injected mixture to flow through the first column by means of a pressurized stream of an inert gas, so that at least one minor component is chromatographically separated from a fraction of the total mixture;

eluting a volume of mixture containing said at least one separated minor component from a second end of the first column; and flowing said eluted volume through one or more additional columns in a similar fashion to obtain additional separation of the one or more minor components.

The invention also provides a gas chromatographic method for separating the isotopic species of hydrogen, comprising:

injecting a sample mixture at a first end of a column which is packed with a molecular sieve material, said column having an initial temperature of about $-185°$ C. to about $-160°$ C.;

causing the injected sample to flow through the column by means of a pressurized stream of an inert gas while increasing the temperature of the column at a rate of up to about 10° C. per hour, so that the various isotopic species contained in the sample are chromatographically separated from one another; and eluting the separated isotopic species from a second end of the column.

Gas chromatographic separation of hydrogen isotopes have been reported in the literature dating from the late 1950's. Basically, three approaches have been employed to effect separations on an analytical scale, and these approaches may be distinguished on the basis of the column packing material used.

It should be noted at the outset that the term "column" as used herein and as it is understood by those skilled in this art, means a tubular structure usually made of metal such as copper or stainless steel which is packed with a material for effecting a separation of gaseous components which are caused to flow therethrough by means of a carrier gas. Columns commonly used for gas chromatography are of a sufficient length that it is often inconvenient to deploy them in a linear fashion. Therefore, gas chromatography columns are frequently formed into spiral coils so that they may be conveniently stored and used, however, linear columns are within the scope of the invention.

Three different column packing materials have been reported for the gas chromatographic separation of hydrogen isotopes. These are molecular sieves used for size exclusion chromatography, alumina used for gas/solid adsorption chromatography, and palladium such as palladium dispersed on alumina used for catalytic adsorption chromatography.

Chromatographic separation of hydrogen isotopes on palladium has been reported for a mixture of $H_2$ and $D_2$ (C. O. Thomas and H. A. Smith, J. Phys. Chem., 63, p. 427 (1959)) using argon as the carrier gas. The separation was carried out in the temperature range 150°-190° C., and the separation efficiency was reported to be poor.

The efficient separation of hydrogen isotopes on alumina has been reported by a number of groups (e.g., J. King Jr. and S. W. Benson, J. Chem. Phys., 44, No. 3, pp. 1007-1014 (1966), H. Weichselgartner et al, Nuclear Tech/Fusion, 4, p. 687 (1983), Frischmuth et al U.S. Pat. No. 4,469,496), and a pilot industrial scale system has been developed.

Alumina used for chromatography is a synthetic polymeric material having a highly active surface. The activity of the alumina may be reduced by moisture and by the incorporation of trace amounts of iron or other metals into the alumina crystal structure. Highly activated alumina can completely adsorb hydrogen at subambient temperatures.

In the systems reported by the Max Planck group, helium was used as the carrier gas and the alumina packed column was maintained at −196° C. with liquid nitrogen. The desirability of operating the column at any temperature other than −196° C. is not suggested by the Max Planck group in their published reports. The separation efficiency was adjusted according to those reports by altering the activity of the alumina used and increasing or decreasing the length of the column.

In contrast to the adsorption type of chromatography inherent in the use of alumina or palladium, chromatography on molecular sieves proceeds on the basis of molecular size. Molecular sieves are synthetic materials usually prepared from sodium or calcium aluminum silicates and are commercially available in beads having pore sizes in the range of 3 to 10 angstroms. The pores in each bead form a network of interconnecting tunnels so that small molecules entering the pores may pass through the network more readily than larger molecules. Thus, a separation of molecular species is accomplished by a sieving effect whereby smaller molecules pass through the sieves faster than larger molecules. Elution is usually in order of increasing molecular size.

Molecular sieves are used commonly in chromatographic applications to separate gases such as helium, hydrogen, argon, oxygen, nitrogen, methane and carbon monoxide. Water, carbon dioxide and hydrocarbons are highly retained by molecular sieves. Oxygen and nitrogen are completely retained by molecular sieves at −50° C. and hydrogen is retained below −180° C.

The separation of hydrogen isotopes on molecular sieves has been reported (S. Akthar and H. A. Smith, "Separation and Analysis of Various Forms of Hydrogen by Adsorption and Gas Chromatography" Chem. Rev., 64, 261-76 (1964); and M. L. Conti and M. Lesimple, J. Chromatog., 19, pp. 32-43 (1967)). While there is no information on the relative capacities of alumina and molecular sieves for chromatographic separations, molecular sieves may be expected to have a greater capacity since the activity thereof is proportional to the volume of the chromatographic bed, whereas the activity of alumina is proportional to the surface area.

The carrier gas for conducting the gas chromatographic separation of hydrogen isotope species on molecular sieves must not interact strongly with the column packing so as to adversely modify the retention of the analytes. This rules out argon which absorbs very strongly on molecular sieves at temperatures below −20° C., however helium or neon do not interact strongly with molecular sieves at temperatures as low as −180° C. and therefore, may be used.

A suitable carrier gas must also have a sufficiently high diffusion rate through the column packing so that the pressure drop across the column is low. This feature reduces the likelihood of leaks forming. Separation of the carrier gas from the separated components must be readily achievable, and the carrier gas must be compatible with the detector means used to monitor the effluent from the column.

From a consideration of the foregoing criteria, helium is the preferred carrier gas for use in the invention.

The chromatographic systems described in the literature use narrow bore analytical columns (2 mm ID) which provide optimum efficiency but minimum capacity (<1 mL chromatographed). The ability of a column to separate components of a mixture is a measure of column efficiency. To be efficient, the gas components must have different affinities for the packing material and sufficient surface area of the packing material must be available to ensure that the gaseous components equilibrate with the surface all the way down the column. As the amount of gas injected onto the column is increased, equilibrium conditions eventually are not satisfied and the column loses efficiency. The point at which a significant loss in efficiency is detected is defined as the column capacity. The loss in column efficiency is manifested in band broadening, decreasing retention times, and changing peak shape. Column capacity depends on the choice of column packing material and the size of the chromatographic bed.

When using the same column packing material, column capacity increases as the square of the column internal diameter. The group at the Max Planck Institute have chromatographed up to 600 mL of gas on 76.2 mm ID columns packed with alumina. Scaling up, however, results in a loss of resolution predicted in chromatography theory by the multi-path component of column efficiency.

In accordance with the present invention, it has been found that in addition to column packing materials and a column scale-up, special chromatographic techniques can be used to obtain a higher column capacity. One of these techniques is called peak cutting. Using this technique in accordance with the present invention, two columns are plumed in series with a valve to allow diversion of the effluent from the first column either to vent or onto the second column. In the case of fusion fuel, early eluters (minor components such as H$_2$, HD and HT) emerging from the first column are allowed to enter the second column along with a portion of the major components. At a preset time, the first column is vented and the effluent saved. The minor components together with a fraction of the major species are then further separated on the second column. Since a significant portion of the gas originally injected is eliminated from the system, the efficiency of separation of the remaining gas components on the second column is improved. The peak cutting technique increases the column capacity while retaining the efficiency of a small diameter column.

Additionally, in accordance with the invention, a plurality of columns may be used to provide peak cutting with respect to separations involving one or more minor components from one or more major components of an isotopic mixture of hydrogen. That is, a partially separated component eluted from a first column may be subjected to further chromatographic separation on one or more additional columns. This embodiment may be used when only a relatively small enrichment may be obtained from separation on each column. The plurality of columns serve to multiply the enrichment factor.

The skilled person will appreciate from a consideration of the following examples that the invention extends to those peak cutting applications involving more than two columns.

EXAMPLES

System Description

A gas chromatography system suitable for purifying and recycling waste gases from a fusion facility includes a carrier gas supply, gas chromatography columns, a temperature controlled container for the columns, flow switching, gas detectors, and carrier gas/hydrogen isotope separation facilities.

Figure 1:
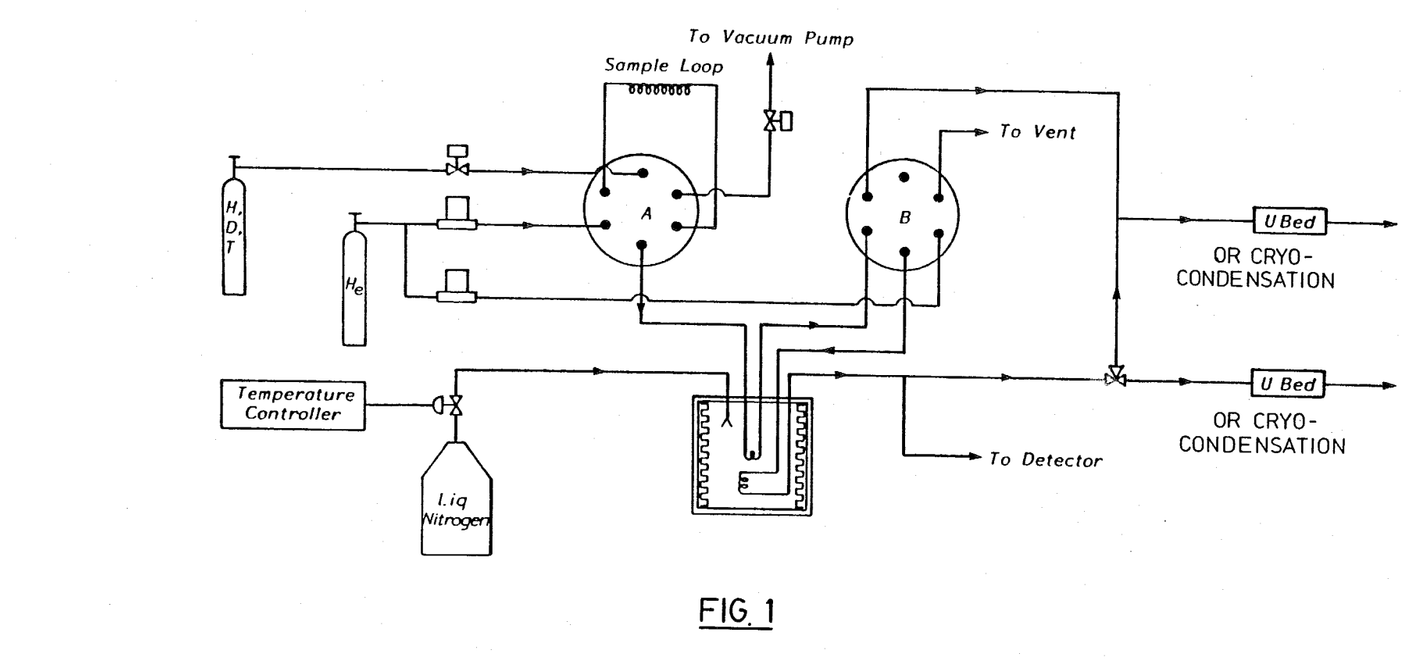
FIG. 1 is a schematic diagram of a gas chromatographic system in accordance with the invention.

The experimental system used to generate the data presented below comprised the following components, and is generally shown in FIG. 1.

Carrier and Sample Gas Supply

1. Helium was the carrier gas and the system was designed for a flow rate of 0.5 to 2 L/min at a pressure of up to 800 kPa (90 psig).
2. Hydrogen isotope gas samples were injected in 100–1000 mL size from a pressurized container. The samples were injected at a pressure of 300 kPa (30 psig) up to 800 kPa (90 psig).
3. The hydrogen sample loop and associated valves were fully tritium compatible.

GC Columns

1. The inside diameter of the GC columns were in the range of 0.8 to 1.9 cm ($\frac{3}{8}''$ to $\frac{3}{4}''$ tubings).
2. Two columns, 0.6 m and 1.5 m long, preferably in the form of coils to minimize the space requirement, were provided.
3. The columns were packed with 5A molecular sieve in the size range of 0.25 to 0.42 mm (40 to 60 mesh).

Temperature Controlled Container

1. The container was sufficiently large for both of the columns and a heating coil.
2. The container was vacuum jacketed for insulation (super insulated stainless steel dewar flask with flange top supplied by Minnesota Valley Engineering, Inc. suitable for this application).
3. The temperature of the container was maintained in the range of $-140°$ C. to $-185°$ C. by spraying liquid nitrogen into the container. The temperature was controlled to $< \pm 1°$ C. of the set point in this temperature range.
4. The container was also heated to 300° C. for 16 hours continuously for not more than once every three months.
5. A temperature controller to control the liquid nitrogen flow and the heater was used.

Gas Detectors

1. A thermal conductivity detector with signal appropriate for operating relays and or motorized valves was used.
2. A flow proportional counting detector ($\beta$-detector) with signal appropriate for operating relays and or motorized valves was used.

Automatic Flow Switching

1. Automatic on-off valve, two six-point valves, and one three-way valve were installed in the system.
2. Controllers to switch the automatic valves to divert the flow to appropriate downstream equipment were used.
3. Signals from the gas detectors were used to control the position of the valves.
4. The response of the valve switching to signal was less than one second.

Carrier Gas/Hydrogen Isotope Separation

1. Uranium beds or cryogenic condensation units would be used to separate the carrier gas (helium) from the hydrogen isotopes.
2. Heaters installed in the uranium beds would be used to desorb the hydrogen isotopes from the bed when required.
3. The carrier gas separation system should be fully tritium compatible.

System Operation

The GC columns were conditioned before they were used to separate hydrogen isotope and re-conditioned every three to four months. The conditioning and normal operation of the column are discussed below.

Conditioning of GC Columns

1. A small flow of helium (e.g., 100 mL/min) was maintained through the columns during conditioning.
2. The container was heated to 275° C. gradually at a rate of 2° C./min and maintained at 275° C. for 14 hours.

Hydrogen Isotope Separation Operation

1. The system was purged with helium for at least ten volumes of the total system.
2. The temperature in the container was controlled to $< \pm 1°$ C. of the desired temperature with liquid nitrogen spraying into the container.
3. The sample loop was pressurized to the desired pressure.
4. The sample was injected into the GC column by switching the six-way valve A automatically (FIG. 1).
5. The flow from the first GC column was connected to the second column initially and then diverted to appropriate carrier gas isotope separation unit by switching the six-way valve B automatically.

6. The flow downstream of the second column would be connected to the appropriate carrier gas/isotope separation unit by automatic valve switching according to the signal from the detectors.

In the laboratory experiments conducted using this system, non-radioactive gases separated in columns were usually vented rather than captured in uranium beds or otherwise separated from the carrier gas. Of course, in a commercial system, the separated components would be recaptured as desired.

Experimental

Figure 2:
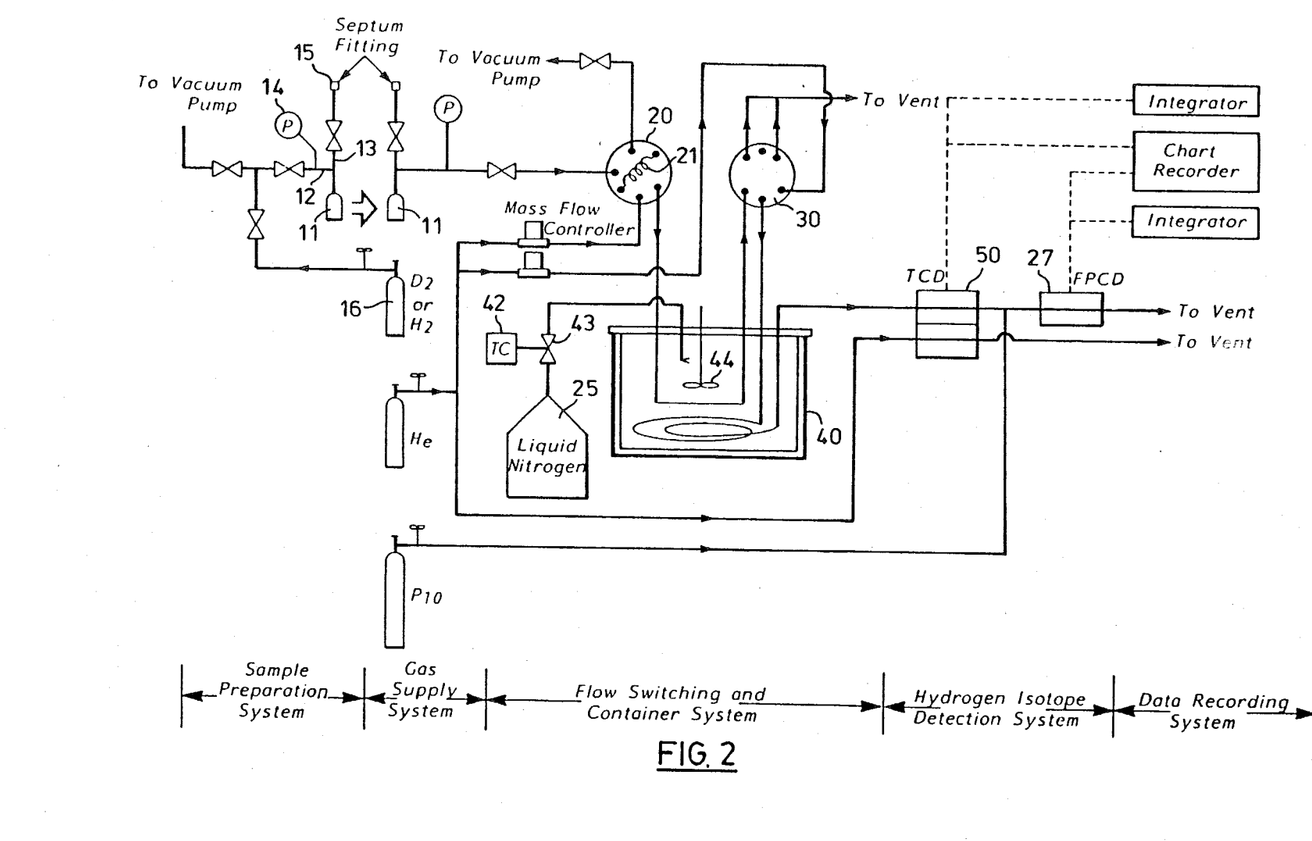
FIG. 2 is a schematic diagram of an experimental gas chromatographic system used to develop the data set out in the examples.

A more detailed schematic diagram of the equipment used is shown in FIG. 2. The system can be divided into five parts, namely, sample preparation, gas supply, column container, gas detection and data recording systems.

In the sample preparation system, hydrogen isotope gas mixtures were prepared in a 1.7 L aluminum cylinder 11. The cylinder 11 was fitted with two entry ports 12 and 13 and a pressure gauge 14. One of the ports 13 was connected to a septum 15 and the other port 12 attached to either a vacuum pump or a high pressure gas cylinder 16. The sample cylinder 11 was evacuated to at least $10^{-2}$ torr. Pure gas components were then introduced into the cylinder by syringes through the septum 15. After addition of appropriate amount of gas, the cylinder 11 was pressurized with either deuterium or hydrogen from the cylinder 16 up to 200 psig. After sample preparation, the cylinder 11 was connected to a six-way valve 20 to fill the sample loop 21 at the desired pressure to be injected to the gas chromatographic columns. For experiments relating to fusion fuel cleanup whereby protium species were removed from the waste fusion fuel, the sample mixture comprised approximately 10% $H_2$, 90% $D_2$ and 2.5 to 5.0 $\mu$Ci/L $T_2$. The pure dimers were equilibrated within the sample cylinder by the addition of a metal catalyst so that all six dimeric isotope species were obtained. For experiments involving temperature programmed separation of all six isotopic species, the sample mixture comprised approximately 50% $H_2$ and 50% $D_2$ with 2.5 to 5.0 $\mu$Ci/L $T_2$ again with catalytic equilibration within the sample cylinder.

In addition to the hydrogen isotope gases supplied in the gas supply system, He, $N_2$, and $P_{10}$ (Ar and $CH_4$ mixture) gases are provided by high pressure gas cylinder. He was the carrier gas for the GC system, $N_2$ was used to pressurize the liquid nitrogen container 25 whereas the $P_{10}$ gas was used in the flow proportional counting detector 27.

Figure 3A:
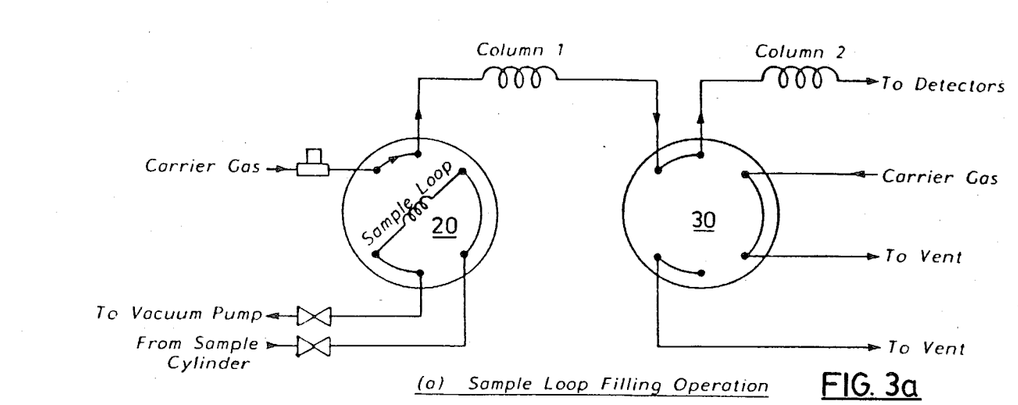
FIGS. 3a, b and c are schematic diagrams of the six way valves used in the systems shown in FIGS. 1 and 2, showing the particular valving arrangements for various stages of the process.

In the flow switching and column container system, the flow switching was carried out mainly by two six way valves 20 and 30. A detailed flow diagram with the two valves 20 and 30 is shown in FIG. 3. Each valve has only two positions allowing each of the six openings to be connected to an adjacent opening. FIG. 3(a) shows the valve 20 position when the sample loop 21 was being filled with gas samples from the sample cylinder 11. In this position, the sample loop 21 was evacuated by closing the valve connected to the sample cylinder 11 and opening the valve to the vacuum pump. Then, the valve to the vacuum pump was closed and the valve connected to the sample cylinder 11 was opened to pressurize the sample loop 21 with the hydrogen isotope sample to the desired pressure.

Figure 3B:
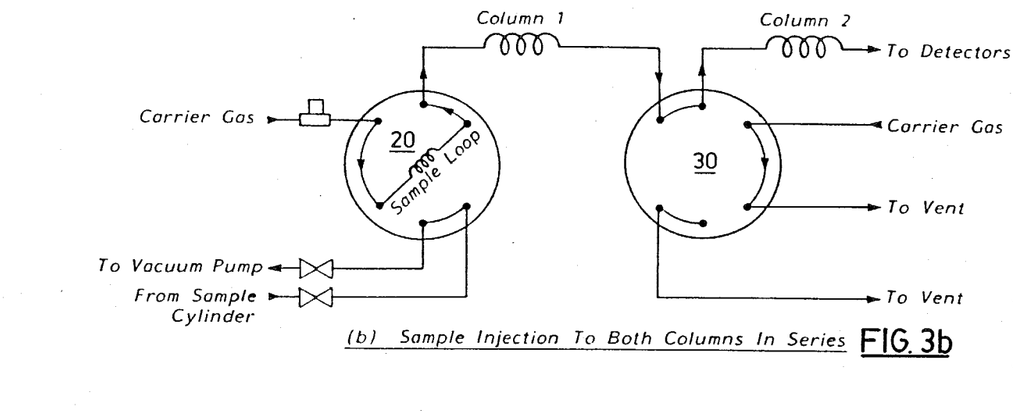

FIG. 3(b) shows the valve positions when the sample in the sample loop 21 was injected to both columns.

Figure 3C:
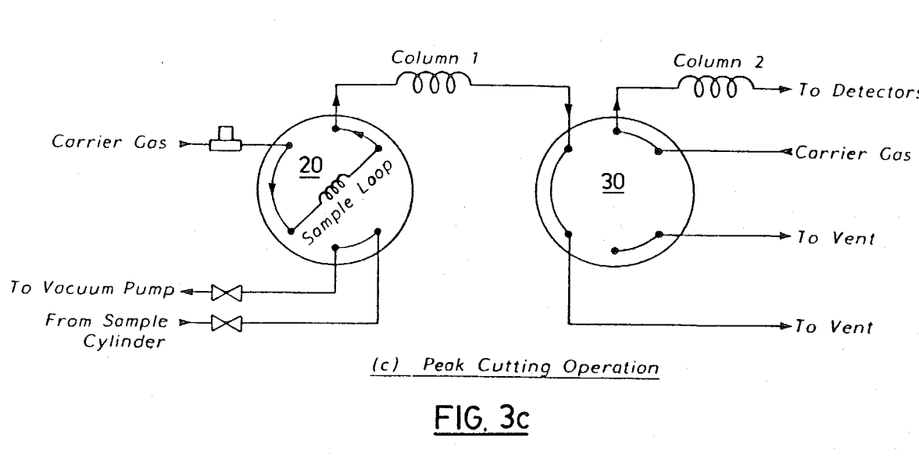

Valve 20 was switched to allow the helium carrier gas to pass through the sample loop 21 to column 1 which was connected to column 2 via valve 30. FIG. 3(c) shows the valve positions when column 1 was "cut to vent". In this flow scheme, the valve 20 position remained unchanged with the carrier gas flowed through the sample loop 21 and column 1. But the position of valve 30 was changed so that the outlet of column 1 was connected to the vent line instead of column 2 and another supply of carrier gas was connected to column 2 to separate the hydrogen isotopes that were loaded onto column 2.

The GC columns were made of stainless steel $\frac{3}{8}''$ tubings (0.8 cm ID). The length of column 1 and 2 were 0.7 m and 1.7 m respectively. Both columns were in the form of a coil with a coil diameter of 10 cm and packed with molecular sieve 5A in the size range of 0.25 to 0.42 mm. The columns were conditioned by passing through a small stream of He through the columns while being heated in an oven. The temperature of the oven was increased gradually at a rate of 2° C./min up to 275° C. and the columns were conditioned for over 15 hours.

Figure 4:
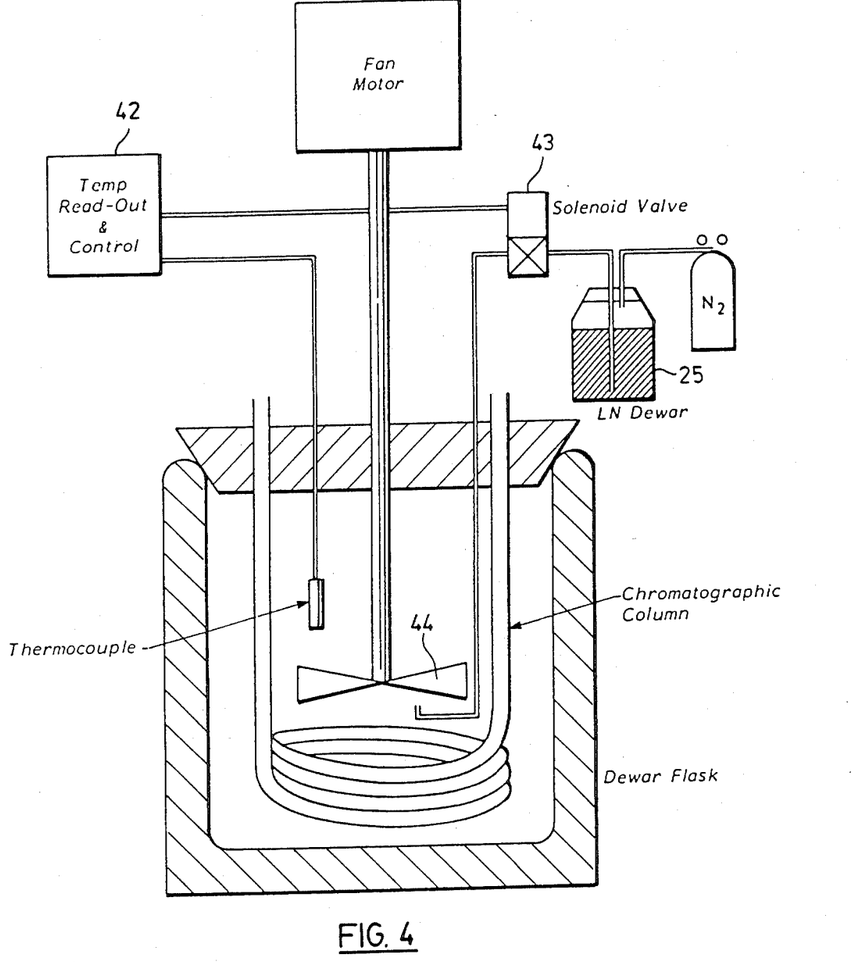
FIG. 4 is a schematic diagram of the column temperature control system used in carrying out the invention.

After conditioning, the columns were placed in a vacuum insulated container 40. A schematic diagram of the container is shown in FIG. 4. The container was cooled by spraying liquid nitrogen into the container and the temperature was controlled by a temperature controller 42 which regulated the flow of liquid nitrogen via a solenoid valve 43. Liquid nitrogen was sprayed into the container near a small fan 44 located at the centre of the container 40. The fan 44 was surrounded by a stainless steel screen (not shown) to avoid direct contact of liquid nitrogen with the columns to ensure even temperature distribution in the columns. A vacuum of $10^{-3}$ torr was maintained between the inner and outer container during the experiment. The top of the container was insulated with a 3.8 cm layer of styrofoam insulation.

Two detectors, namely a thermal conductivity detector 50 and a flow proportional counting detector 27, were used to detect the hydrogen isotope species. The thermal conductivity detector 50 detected $H_2$, HD and $D_2$ only whereas the flow proportional counting detector 27 detected HT, DT and $T_2$ for all the experiments because of the very low concentration of the tritiated species. Signals from the two detectors were recorded by a dual pen recorder and integrated by two integrators.

Experimental Procedure

The experimental procedures for each experiment were as follows.

Cooling of the Column Container

Liquid nitrogen was supplied by a 55 L container 25 connected to the solenoid valve 43 and the column container 40. The temperature controller 42 was then set to the desired temperature. It usually took 1.5 to 2 hours to cool the column container 40 from room temperature to $-140°$ C. to $-180°$ C.

Sample Loop Filling

To fill the sample loop 21 with the hydrogen isotope mixture, the position of the six way valve 20 was as shown in FIG. 3(a). The sample loop was evacuated by opening the valve leading to the vacuum pump. After the sample loop 21 was evacuated, the valve to the vacuum pump was closed and the loop was filled with the gas sample to the desired pressure by opening the valve on the sample cylinder 11 connected to the six-way valve 20.

Sample Injection Through Both Columns

To inject the sample in the sample loop, the six-way valve 20 was switched so that the carrier gas passed through the sample loop 21 and flushed the sample to the two columns connected in series through the six-way valve 30 (see FIG. 3(b)). The gas sample was then separated in both columns.

Peak Cutting Operation

After the sample was injected and all the H-containing components ($H_2$, HD and HT) was eluted from column 1, the six-way valve 30 was switched so that the outlet of column 1 was released to vent and a separate carrier gas supply was connected to column 2 to continue the separation of hydrogen isotopes on column 2 (see FIG. 3(c)). By this operation, a large fraction of the major components $D_2$, DT and $T_2$ can be diverted from column 1 to storage and the amount of hydrogen isotopes loaded on the second column could be significantly reduced to improve the separation of the isotopes by this column. In the particular trials conducted pursuant to the described experimental procedure for fusion fuel clean-up, the fraction of major components diverted from column 1 to storage generally exceeded 60% of the total volume of the mixture injected. However, it will be clear to the person skilled in this art that the peak cutting procedure always results in an enrichment of the minor components contained in the fraction injected onto the second column. In those instances when the enrichment factor is relatively low, i.e., where relatively little separation occurs on the first column, it will be necessary to use several columns in series to obtain the desired results.

Various experimental parameters have been studied including column diameter, column length, temperature, sample size, and peak cutting operation. The main objective of the experimental program was to maximize the throughput and separation of the isotope species. The following selected results illustrate the effect of the experimental parameters on throughput and separation.

Column Diameter and Length

Different column packings were tested and molecular sieve 5A was selected and used in most of the experiments. Initial experiments were carried out with a small ⅛" (2 mm) tubing column and ⅜" (8 mm) tubing columns were used in most of the subsequent experiments. Larger columns (1.9 cm and 2.5 cm) were also tested briefly. Larger samples could be separated in larger columns. However, when a larger diameter column was used, a longer column (longer residence time) or lower temperature was required to maintain the separation. Overall, results from the various diameter columns seemed to indicate that the throughput increased linearly with the column diameter and the ⅜" (8 mm) column was found to be adequate for a throughput of 1 L/h or more. The length of the ⅜" columns required was found to be 2' (0.6 m) and 5' (1.5 m) to provide adequate separation of the isotopes. While separations using 2 and 8 mm columns were satisfactorily effected in the temperature range of −160° to −140° C. it was noted that an increase in column diameter may require a lower temperature, perhaps as low as about −180° C., in order to maintain adequate separation of the isotopes.

Temperature Effect

The temperature of the columns was varied from −145° C. to −160° C. Experimental results showed that temperature had a very significant effect on the elution time of the hydrogen isotope species (i.e., the time interval during which the hyrogen isotopes were emerging from the outlet of the GC column) and the separation of the hydrogen isotopes. A summary of some of the selected experimental results is given in Table 1 for the 8 mm columns. For a sample size of 250 mL, the elution time increased from 7.5 min at −148° C. to 19.4 min at −155° C. and 27.0 min at −160° C. The elution time was increased by a factor of approximately 2 for a decrease of every 5° C. in temperature. The increase of elution time led to a decrease of throughput from 2 L/h at −148° C. to 0.56 L/h at −160° C. However, the separation was poor at −148° C. and a temperature of −150° C. or lower was necessary to achieve adequate separation. For example, at −150° C., a decontamination factor (DF) (see Table 1) of 2 for protium species was reached. By lowering the temperature to −160° C., the DF was increased to 14.

Effect of Peak Cutting

Applying the peak cutting technique, the throughput was increased somewhat due to the slight decrease in elution time by peak cutting. For example, at −150° C. and for a sample size of 250 mL, the elution time was decreased from 10 min without peak cutting to 8.5 min with peak cutting. The most significant improvement of peak cutting, however, was on the DF. At −150° C. the DF was increased from 2 to 60 by peak cutting and at −160° C. from 14 to 150 (see Table 1).

Effect of Sample Size

As expected, increasing the sample size increased the throughput but reduced the DF with or without peak cutting. For example, at −150° C., the throughput was only 0.3 L/h but the DF was 150 for a sample size of 50 mL. Increasing the sample size to 250 mL increased the throughput to 1.5 L/h but the DF was reduced to 2.

Optimization of Column Operation

Although very high throughput and good DF were achieved at −150° C., the elution time was relatively short, i.e., 8.5 min. Precise timing of the valve switching is required to minimize the error in peak cutting and relatively frequent valve switching is also required to operate the column at this temperature. A series of experiments was carried out to increase the elution time by operating the column at −155° C., and increasing the sample size. It was found that at −155° C., with peak cutting, a throughput of 1.8 L/h was achieved with acceptable separation of the isotope species at a sample size of 740 mL. The elution time was about 25 min which will reduce the frequency of valve switching significantly. Increasing the sample size to 1000 mL resulted in a poor separation of the isotope species and a decrease in the throughput. Hence, a sample size of 740 mL seemed to be close to the optimum sample size for the columns used in the system.

TABLE 1

Summary of Selected Experimental Results
for the 8 mm 0.6 m + 1.5 m Columns

| Temperature (°C.) | Sample Size (mL) | Elution Time (min) | Through-put (L/h) | Decontamination* Factor | Peak Cutting |
|---|---|---|---|---|---|
| −148 | 254 | 7.5 | 2.0 | — | No |
| −150 | 50 | 10.0 | 0.3 | 150 | No |
| −150 | 250 | 10.0 | 1.5 | 2 | No |
| −150 | 50 | 7.0 | 0.43 | 300 | Yes |
| −150 | 250 | 8.5 | 1.8 | 60 | Yes |
| −155 | 254 | 19.4 | 0.79 | — | No |
| −155 | 740 | 29.8 | 1.5 | — | No |
| −155 | 740 | 24.8 | 1.8 | — | Yes |
| −155 | 1000 | 42.8 | 1.4 | — | No |
| −155 | 1000 | 43.8 | 1.4 | — | Yes |
| −160 | 250 | 27.0 | 0.56 | 14 | No |
| −160 | 250 | 26.8 | 0.56 | 150 | Yes |

*Decontamination Factor (DF) = $\dfrac{\text{fraction of the H-containing species in the feed}}{\text{fraction of the H-containing species in the product}}$ The peak cutting technique requires smaller internal diameter and shorter columns than is the case when a single column is used, and in the case of fusion fuel clean-up, the chromatographic system can be built around a commercial gas chromatograph. The ancillary equipment such as detectors, flow controllers, switching values and connecting tubing are stock equipment and the 8 mm columns are easily made by chromatographic supply houses.

The high efficiency gas chromatographic peak cutting technique of the invention is most beneficial when minor components are to be separated from a major component. Clean-up of protium from fusion fuel, tritium waste treatment and emergency tritium clean-up are perfect applications for peak cutting gas chromatography. When two major gas components are to be separated, the relatively low capacity of gas chromatography becomes the gas processing rate controlling factor. In this case either much longer and wider columns must be employed or the separation scheme may be more efficiently carried out by cryogenic distillation possibly followed by high efficiency gas chromatography.

Temperature Programming

The system shown in FIGS. 1–4 and described above may be used to effect a full separation of all six isotopic species of hydrogen using temperature programming on a single column. In this regard a column having an inside diameter of 2 cm with a length of 7.5 m was used. The column was packed with 5A molecular sieves, and He was used as the carrier gas. A 2 L sample of a gas mixture comprising 50% $H_2$, 50% $D_2$ and 2.5 to 5.0 $\mu$Ci/L $T_2$ was used in each trial. The pure dimers were equilibrated catalytically in the sample cylinder to give all six isotope species.

The column was cooled to as low as −186° C. and the 2 L sample mixture was injected. The He carrier gas was maintained at a flow rate of 4 L/min at a pressure of about 300 kPa measured just upstream of the column. The column temperature was increased at a rate varying up to 10° C. every 60 min to a final temperature near −150° C. Selected results for experiments giving similar isotope separations are summarized in Table 2 compared with the results obtained at a constant temperature of −166° C. At −166° C., separation of all components was completed in about 330 min. There was overlapping of some of the components at this temperature, hence the sample would have to be partially recycled.

The net throughput was estimated to be about 270 mL/h or 135 mL/h/1 cm column. When temperature programming was applied, the elution time was reduced to as low as 130 min corresponding to a net throughput of about 770 mL/h or 380 mL/h/1 cm column which is more than five times the reported throughput of 50–75 mL/h/1 cm column reported by the Max Planck group.

TABLE 2

Selected Experimental Results for the
2 cm 7.5 m Column With Similar Isotope
Separation for a Hydrogen Sample of 2 L

| Initial Temp. °C. | Rate of Temp. Change °C./h | Final Temp. °C. | Elution Time of $H_2$ - DT (min) | Estimated Net Throughput (mL/h) |
|---|---|---|---|---|
| −166 | 0 | −166 | 330 | 270 |
| −170 | 3 | −155 | 170 | 600 |
| −172 | 5 | −152 | 130 | 770 |
| −184 to −186 | 10 | −154 | >180 | <570 |

These results indicate that separation of hydrogen isotope species using the temperature programming method of the invention enables one to obtain a much greater throughput for the separation of hydrogen isotopes than was previously thought possible. The invention provides a viable alternative to processing hydrogen isotope mixtures by cryogenic distillation.

Isotope Storage

The standard technique for dealing with separated hydrogen isotope species involves storage in a bed of a suitable powdered metal. Powdered uranium beds are commonly used in this regard, and the hydrogen species absorbed thereon are usually stored at room temperature. The ability to absorb hydrogen onto uranium powder also provides a means for separating the isotope species from the carrier gas which is not so absorbed.

While this method of separation from the carrier gas and storage is suitable for $H_2$, $D_2$ or $T_2$ species, it will not allow the mixed dimers to maintain their integrity due to the catalytic effect provided by the metal absorbent. Thus, HD absorbed onto uranium quickly equilibrates to form a mixture of $H_2$, HD and $D_2$. In order to avoid this equilibration of mixed dimeric species, the present invention includes the step of separating and storing such mixed dimers at low temperature free of catalyzing metals.

This feature of the invention takes advantage of the fact that hydrogen and its various isotopic species condense at about 20K, while helium does not condense until about 4K. Therefore, fractions eluted from the GC system in accordance with the invention may be separated from the helium carrier gas and captured for storage by cooling the effluent to about 15K. In particular, the mixed species, i.e. HD, DT and HT may be captured and stored in pure form free from equilibration by using this technique.

We claim:

1. A gas chromatographic method for separating one or more minor components from one or more major components of an isotopic mixture of hydrogen, comprising:
    injecting a volume of the mixture at a first end of a first of a plurality of columns which are packed with a molecular sieve material, each column being maintained at a temperature of from about −180° C. to about −140° C.;

causing the injected mixture to flow through the first column by means of a pressurized stream of an inert gas, so that at least one minor component is chromatographically separated from a fraction of the total mixture;

eluting from a second end of the first column at least one volume of mixture containing an enriched concentration of said at least one separated minor component as compared to the original mixture injected; and flowing said eluted volume through at least one more column so that chromatographic separation of the one or more minor components from the one or more major components is obtained.

2. A method as claimed in claim 1, wherein the molecular sieve material is a sodium or calcium aluminum silicate.

3. A method as claimed in claim 1, wherein the molecular sieve material is of the type 5A having a pore size of 5 angstroms.

4. A method as claimed in claim 3, wherein the molecular sieve material comprises beads having diameters in the range 0.25 to 0.42 mm.

5. A method as claimed in claim 1, wherein the carrier gas is helium.

6. A method as claimed in claim 5, further comprising the step of separating the separated isotopic components from the carrier gas, wherein the $H_2$, $D_2$ and $T_2$ components are absorbed on separate uranium beds, and the HD, HT and DT components are condensed out of the carrier gas and stored at about 15K.

7. A method as claimed in claim 1, wherein each column is maintained at a temperature of from about $-170°$ C. to about $-140°$ C.

8. A method as claimed in claim 1, wherein each column is maintained at a temperature of from about $-160°$ C. to about $-140°$ C.

9. A method as claimed in claim 1, wherein at least one minor component is chromatographically separated from at least 25% by volume of the total mixture in the first column.

10. A method as claimed in claim 1, wherein at least one minor component is chromatographically separated from at least 40% by volume of the total mixture in the first column.

11. A method as claimed in claim 10, wherein at least one minor component is chromatographically separated from at least 60% by volume of the total mixture in the first column.

12. A method as claimed in claim 1, wherein the carrier gas pressure is in the range 100-800.

13. A gas chromatographic method for separating protium containing species from an isotopic mixture of hydrogen used for a fusion fuel, comprising the steps of:

injecting a volume of the mixture at a first end of a first column which is packed with a molecular sieve material, the column being maintained at a temperature of from about $-180°$ C. to about $-140°$ C.;

causing the injected mixture to flow through the first column by means of a pressurized stream of an inert gas, so that the protium containing isotopic species are chromatographically separated from a fraction of the total amount of $D_2$, DT and $T_2$ isotopic species;

eluting a first fraction from a second end of the first column, said first fraction containing substantially all of the protium containing isotopic species;

injecting the first fraction at a first end of a second column which is packed with a molecular sieve material, the column being maintained at a temperature of from about $-180°$ C. to about $-140°$ C.;

eluting a second fraction from the second end of the first column, said second fraction comprising a mixture of $D_2$, DT and $T_2$ isotopic species;

causing the first fraction to flow through the second column by means of a pressurized stream of an inert gas, so that the various isotopic species contained in the fraction are chromatographically separated from one another; and eluting the separated isotopic species from a second end of the second column.

14. A method as claimed in claim 13, wherein the molecular sieve material is a sodium or calcium aluminum silicate.

15. A method as claimed in claim 13, wherein the molecular sieve material is of the type 5A having a pore size of 5 angstroms.

16. A method as claimed in claim 15, wherein the molecular sieve material comprises beads having diameters in the range 0.25 to 0.42 mm.

17. A method as claimed in claim 13, wherein the carrier gas is helium.

18. A method as claimed in claim 13, wherein the carrier gas pressure is in the range 100-800 kPa.

19. A method as claimed in claim 13, wherein the first and second columns are maintained at a temperature of from about $-170°$ C. to about $-140°$ C.

20. A method as claimed in claim 13, wherein the first and second columns are maintained at a temperature of from about $-160°$ C to about $-140°$ C.

21. A method as claimed in claim 13, wherein at least one minor component is chromatographically separated from at least 25% by volume of the total mixture in the first column.

22. A method as claimed in claim 13, wherein at least one minor component is chromatographically separated from at least 40% by volume of the total mixture in the first column.

23. A method as claimed in claim 13, wherein at least one minor component is chromatographically separated from at least 60% by volume of the total mixture in the first column.

24. A gas chromatographic method for separating the isotopic species of hydrogen, comprising:

injecting an isotopic mixture at a first end of a column which is packed with a molecular sieve material, said column having an initial temperature between about $-185°$ C. and about $-170°$ C.;

causing the injected sample to flow through the column by means of a pressurized stream of an inert gas while increasing the temperature of the column at a rate of up to about 10° C. per hour, so that the various isotopic species contained in the mixture are chromatographically separated from one another; and eluting the separated isotopic species from a second end of the column.

25. A method as claimed in claim 24, wherein the molecular sieve material is a sodium or calcium aluminum silicate.

26. A method as claimed in claim 24, wherein the molecular sieve material is of the type 5A having a pore size of 5 angstroms.

27. A method as claimed in claim 26, wherein the molecular sieve material comprises beads having diameters in the range 0.25 to 0.42 mm.

28. A method as claimed in claim 24, wherein the carrier gas is helium.

29. A method as claimed in claim 24, wherein the carrier gas pressure is in the range 100–800 kPa.

30. A method as claimed in claim 24, further comprising the step of separating the separated isotopic components from the carrier gas, wherein the $H_2$, $D_2$ and $T_2$ components are absorbed on separate uranium beds, and the HD, HT and DT components are condensed out of the carrier gas and stored at about 15K.

31. A method as claimed in claim 24, wherein the column temperature does not exceed about $-145°$ C.

* * * * *